(12) United States Patent
Fakhim et al.

(10) Patent No.: US 11,272,834 B2
(45) Date of Patent: Mar. 15, 2022

(54) IMAGING SYSTEM AND METHOD FOR QUALITY AND DOSAGE CONTROL OF ANESTHETICS APPLIED BY A SPRAY NOZZLE

(71) Applicant: AIMIC Corp., Toronto (CA)

(72) Inventors: Bamdad Fakhim, Tehran (IR);
Mohammadreza Rezaei, Tehran (IR);
Vahid Asnaashari, Tehran (IR);
Mohammad Moshfegh, Tehran (IR);
Nasser Ashgriz, Thornhill (CA)

( * ) Notice: Subject to any disclaimer, the term of this patent is extended or adjusted under 35 U.S.C. 154(b) by 0 days.

(21) Appl. No.: 17/227,746

(22) Filed: Apr. 12, 2021

(65) Prior Publication Data

US 2021/0315449 A1    Oct. 14, 2021

Related U.S. Application Data

(60) Provisional application No. 63/008,984, filed on Apr. 13, 2020.

(51) Int. Cl.
| | |
|---|---|
| *A61B 1/267* | (2006.01) |
| *A61B 1/05* | (2006.01) |
| *A61B 1/00* | (2006.01) |
| *A61B 1/06* | (2006.01) |

(Continued)

(52) U.S. Cl.
CPC .......... *A61B 1/267* (2013.01); *A61B 1/00009* (2013.01); *A61B 1/00032* (2013.01); *A61B 1/00066* (2013.01); *A61B 1/015* (2013.01); *A61B 1/05* (2013.01); *A61B 1/06* (2013.01); *A61M 5/30* (2013.01); *A61M 2202/048* (2013.01)

(58) Field of Classification Search
CPC ....... A61B 1/267; A61B 1/015; A61B 90/361; A61M 5/30; A61M 2202/048; A61M 11/00; A61M 11/007; A61M 11/06; A61M 11/008; B05B 12/004; G06K 9/4642; G01M 9/067; G01N 15/0227; G01N 15/0023; G01N 15/0205; G01N 29/4427
See application file for complete search history.

(56) References Cited

U.S. PATENT DOCUMENTS 4,432,350 A * 2/1984 Breslau ................. A61M 19/00
600/187
5,571,071 A * 11/1996 Shapiro .................. A61B 1/267
600/185

(Continued)

OTHER PUBLICATIONS

Eslamian, Morteza & Ashgriz, Nasser. (2011). Swirl, T-Jet and Vibrating-Mesh Atomizers. 10.1007/978-1-4419-7264-4_33 (Year: 2011).*

(Continued)

*Primary Examiner* — Timothy J Neal
*Assistant Examiner* — Genja M Frankert
(74) *Attorney, Agent, or Firm* — Nasser Ashgriz; UIPatent Inc.

(57) ABSTRACT

A device to check the quality and dosage of anesthetic dispensing device that is used for the application of anesthetic fluids using a spray nozzle is provided. This device can be adapted for use in the oral cavity and upper tracheal area of a medical patient prior to intubation of such patient. The present device comprises of a camera system, a stroboscopic lighting system, and an image analysis software.

17 Claims, 14 Drawing Sheets

(51) Int. Cl.
*A61M 5/30* (2006.01)
*A61B 1/015* (2006.01)

(56) References Cited

U.S. PATENT DOCUMENTS

| | | | | |
|---|---|---|---|---|
| 2006/0149129 | A1* | 7/2006 | Watts | A61B 1/0676 600/113 |
| 2010/0094090 | A1* | 4/2010 | Mejia | A61B 1/042 600/120 |
| 2010/0179511 | A1* | 7/2010 | Rajan | A61M 35/003 604/514 |
| 2011/0028790 | A1* | 2/2011 | Farr | A61B 1/24 600/187 |
| 2011/0048414 | A1* | 3/2011 | Hoekman | A61M 15/00 128/200.23 |
| 2011/0190689 | A1* | 8/2011 | Bennett | A61B 1/00016 604/21 |
| 2012/0116222 | A1* | 5/2012 | Sawada | A61B 17/320068 600/439 |
| 2012/0149643 | A1* | 6/2012 | Fein | A61P 13/02 514/10.9 |
| 2012/0178997 | A1* | 7/2012 | Tydlaska | A61B 1/00105 600/186 |
| 2015/0092189 | A1* | 4/2015 | Waters | G01N 21/53 356/213 |
| 2015/0099934 | A1* | 4/2015 | Sartore | A61B 1/267 600/187 |
| 2015/0112146 | A1* | 4/2015 | Donaldson | A61B 1/00032 600/188 |
| 2015/0165136 | A1* | 6/2015 | Galgon | A61M 11/007 128/200.14 |
| 2015/0173598 | A1* | 6/2015 | Alexander | A61B 1/00154 600/187 |
| 2016/0206189 | A1* | 7/2016 | Nearman | A61B 1/267 |
| 2017/0065990 | A1* | 3/2017 | Gopalan | B05B 11/30 |
| 2017/0189923 | A1* | 7/2017 | Timms | B05B 11/046 |
| 2017/0209022 | A1* | 7/2017 | Molnar | A61M 16/0465 |
| 2018/0220882 | A1* | 8/2018 | Ghorbanian | A61B 1/07 |
| 2018/0310378 | A1* | 10/2018 | Kwok | A61B 1/0684 |
| 2019/0049559 | A1* | 2/2019 | Hien | B05B 12/008 |
| 2019/0274533 | A1* | 9/2019 | Attinger | A61B 1/267 |
| 2021/0106777 | A1* | 4/2021 | Decock | A61M 15/08 |
| 2021/0137376 | A1* | 5/2021 | Vargo | A61B 1/00029 |
| 2021/0199552 | A1* | 7/2021 | Van Oostrum | G06T 5/50 |

OTHER PUBLICATIONS

Manin, Julien, and William D. Bachalo 2020. "Advances in Imaging Diagnostics for Spray and Particle Research in High-Speed Flows" Applied Sciences 10, No. 4: 1450. https://doi.org/10.3390/app10041450 (Year: 2020).*

* cited by examiner

IMAGING SYSTEM AND METHOD FOR QUALITY AND DOSAGE CONTROL OF ANESTHETICS APPLIED BY A SPRAY NOZZLE

FIELD OF THE INVENTION

The present invention relates to medical imaging devices, and more particularly, to imaging devices for laryngoscopy and to methods that apply a liquid to the interior parts of a patient, such as to the trachea area.

BACKGROUND OF THE INVENTION

Endotracheal intubation procedures are performed on certain medical patients. In this procedure, a tube providing an airway may be introduced to assist the breathing of a patient having undergone certain kinds of trauma. The anesthetic laryngoscope is an essential tool for the implementation of cardiopulmonary resuscitation. In this process, a laryngoscope blade is inserted into the mouth and is used to retract soft tissue, opening the patient's jaw and mouth to form a clear, open path through which a tube or instrument may be inserted.

There are a wide variety of laryngoscopes with different designs and shapes. They generally consist of a handle, a blade and a light source. Blades come in a wide variety of shapes, tip designs, and different lighting systems. Blades generally have a spatula section that contacts the tongue and a flange. The proximal vertical flange is sometimes called the vertical step. At the base (or heel) of the blade is the block, which interacts with the top of the handle. Blades are designed to attach and detach from the handle with a standardized fitting (usually engaged at 45 degrees) that connects a hook on the blade to a small rod at the top of the handle. In many systems, the connection between the blade and handle causes the light to come on when the blade is opened.

Most laryngoscope blades are made from steel and most are chrome plated. There are also plastic blades that can also be fiber-lit using acrylic rod for light guides.

The spatulate of the blade is axially curved to cooperate with the conventional shape of oral cavity structure. The curved spatula portion of the blade is used for retracting soft tissue and opening the patient's jaw and mouth to form a clear, open path through which a tube or instrument may be inserted. The wide variety of laryngoscopes differ mainly in design and accessories.

In those cases where the patient is unconscious, there is no patient gag reflex over which the medical practitioner must surmount to install a tube, or to insert some other medical device. Consequently, difficulty of an intubation procedure is greatly reduced, although not eliminated. However, there exist instances where the patient is awake, at least partially alert, desirably remains in such condition for a further period of time, and prompt intubation must be performed in spite of such facts. In such cases, the patient's own gag reflex can constitute a significant obstacle to intubation.

Conscious endotracheal intubations are typically accomplished using a fiber optic guide, and require anesthetizing the oral cavity, oropharynx, tonsillar pillars, base of the tongue, supraglottic region and vocal cords, and other deep pharyngeal structure, such as the deep posterior pharyngeal wall, pyriform fossa on either side of the larynx, vallecula, and the proximal trachea. Anesthetization typically starts with topical application of anesthetic fluid at the front of the oral cavity, and then progresses inward toward the tracheal-esophageal bifurcation area. Typically, an area will be numbed prior to moving on to the next deeper area. Unfortunately for the patient, each new area receiving anesthetic initially presents a new stimulated area to promote a gag reflex.

It is generally desirable to apply anesthetic agent in a substantially uniform coating to reduce waste and avoid over- or under-medication. Application of anesthetic topically by way of a transfer medium, such as a sponge, often produces a substantially non-uniform coating of agent on the patient's tissue, as well as physically imposing on non-anesthetized areas. Squirting anesthetic agent from the nozzle of a syringe, e.g., as a jet, is equally unsatisfactory, and also wasteful. Even systems with misting nozzles may not properly apply the anesthetic fluid. Currently, a practitioner has no mean to determine whether the fluid is applied properly in all desired areas for an endotracheal intubation procedure.

BRIEF SUMMARY

The present invention is a new laryngoscopy system that has an anesthetic applicator and an imaging system that can determine whether the anesthetics are applied properly. The presently disclosed laryngoscopy system not only applies anesthetic fluid but also it has an imaging system to determine the quality of the application of the anesthetics. It allows for application of anesthetic as a more uniform coating to resist over-, or under-medicating the patient. It further provides direct observation of the application of the anesthetic agent on the oral cavity, oropharynx, tonsillar pillars, base of the tongue, supraglottic region and vocal cords, and other deep pharyngeal structure, such as the deep posterior pharyngeal wall, pyriform fossa on either side of the larynx, vallecula, and the proximal trachea.

The presently disclosed laryngoscope has an anesthetic dispenser assembly that includes a fluid dispensing device with a spray nozzle to spray an anesthetic fluid on the inner surfaces of a patient oropharyngeal tissues. The application of topical anesthetic in a misted form minimizes the amount of required anesthetic agent, produces a more uniform and better-dispersed coating of anesthetic agent, minimizes irritation to patient tissue during application of the anesthetic agent, and reduces likelihood of accidentally overdosing the patient, or causing patient lung-trauma resulting from aspiration of anesthetic fluid. A syringe is operably connected to the fluid dispensing nozzle to permit dispensing a dose of fluid in a form of a mist onto a patient's oropharyngeal tissue by depressing the plunger of the syringe. The syringe is connected to the nozzle by a tubing.

Currently, the practitioners randomly orient the spray nozzle and try to coat all airway areas. This results in significant loss of anesthetic, over-coating in some areas, and undercoating in others, and also slows effectiveness of the drug. The present device allows the practitioner to realize where the spray is being applied to and what is the coating conditions. The system has a mechanism to easily change the orientation of the nozzle and the spray.

The invention may be embodied to provide an anesthetic dispenser assembly including a holder having a handle operably connected to a proximal end of the blade of the laryngoscope that is adapted for insertion into the mouth of a medical or veterinary patient to dispose the blade's distal end in proximity to the patient's oropharyngeal tissue. The anesthetic dispenser assembly also includes a fluid dispensing device carried near the distal end of the retractor. The present device has a spray nozzle to spray an anesthetic fluid on the inner surfaces of a patient oropharyngeal tissues.

In one embodiment, the spray nozzle can be oriented (rotated or pivoted) in different directions to change the direction of the spray.

In certain embodiments of the apparatus structured as described herein, a holder is attached to the handle to hold the syringe in the proximity of the procedure. For ease of operation, an automatic syringe is used to spray a known amount of fluid at a certain pressure with only a push of a button.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF THE INVENTION

The present device is a laryngoscope in operation with a fluid dispensing device and a visualization system to validate the application of the spray formed by the spray.

Figure 1A:
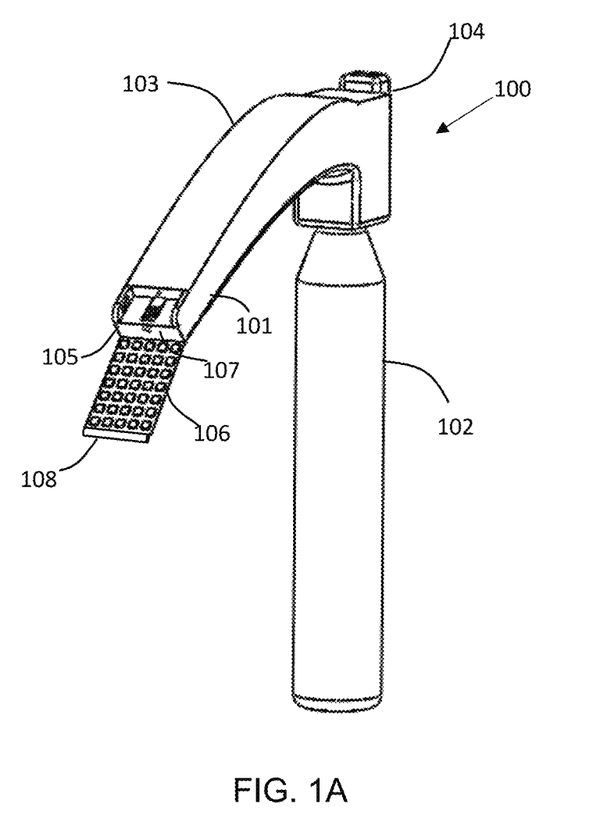
FIG. 1A is a perspective view of the first embodiment of the present anesthetic laryngoscope with an anesthetic applicator and imaging system.
Figure 1B:
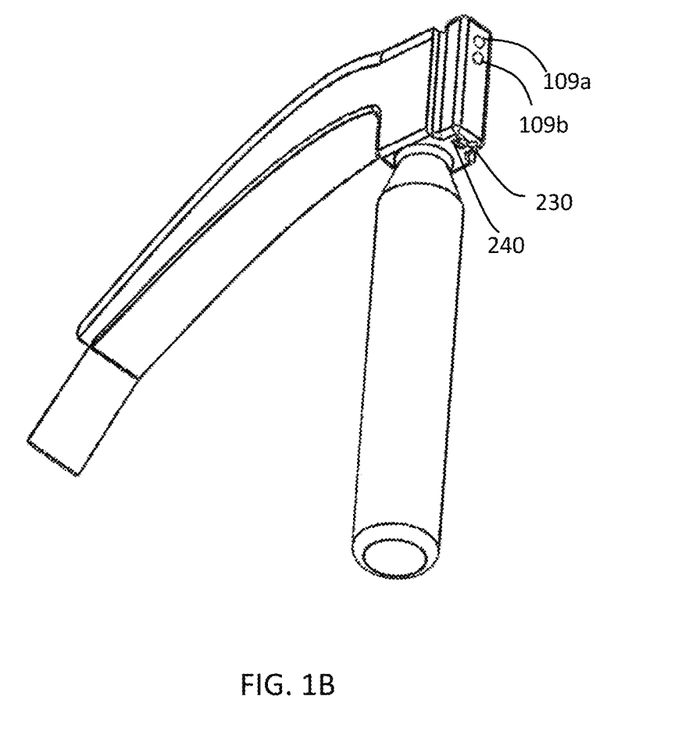
FIG. 1B is a second perspective view of the first embodiment of the present anesthetic laryngoscope with an anesthetic applicator and imaging system.
Figure 1C:
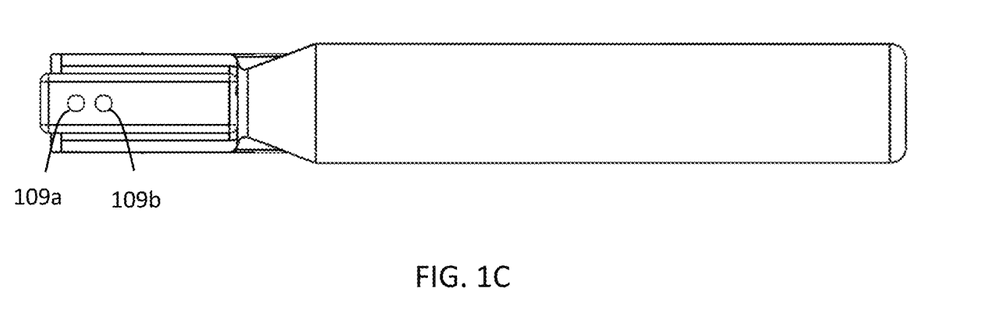
FIG. 1C is the rear view of the first embodiment of the present anesthetic laryngoscope with an anesthetic applicator and imaging system.
Figure 2A:
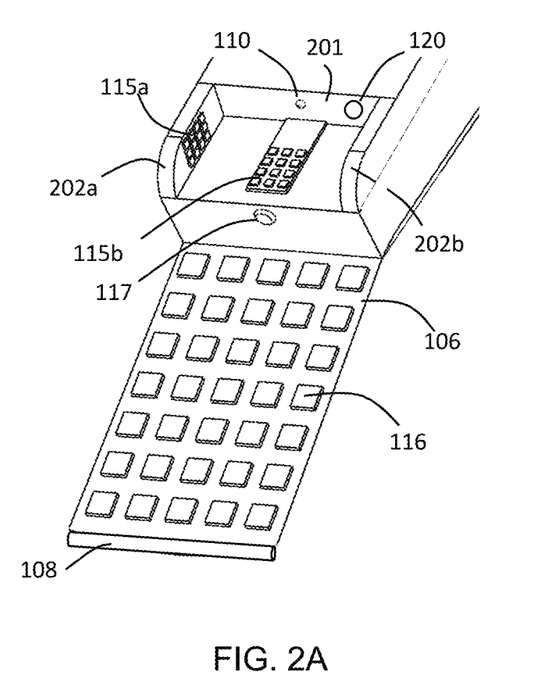
FIG. 2A is a close-up view of the spatula and the tip of body of the blade of the present anesthetic laryngoscope with the location of the camera being on the tip of the body of the blade.

FIG. 1A-1C show one embodiment of the present device. Device 100 comprises of a blade 101 and a holder 102. The blade 101 has a body 103 that has a proximal end 104 and a distal end 105. A retractor 106 is attached to the distal end of the body 103 of the blade. The retractor can be permanently, removable or flexibly attached to the blade. In the embodiment shown in FIGS. 1A and 2A, the distal end of the body 105 has a front step 201 and side lips 202a and 202b. As illustrated in FIG. 2A, the present device has a spray nozzle 110 designed to apply topical local anesthetic agent to oropharyngeal tissues of a patient. The spray nozzle is in communication with the fluid inlet 230 as illustrated in FIG. 1B, to which a flexible line or a syringe can be attached to. A fluid channel (not shown) can be part of the internal structure of the body or it can be a fluid line set externally on the body of the blade. The spray nozzle 110 can generate a spray of fluid droplets. The spray nozzle is replaceable and it may have a structure to orient the discharge direction of the nozzle.

A lighting system, preferably comprising of a set of LED lights, 115a in FIG. 2A, located on the side lip 202a allows imaging of the spray by the spray camera 120 (the first camera) that is located on the front step 201. The spray camera is configured for closeup imaging with high magnification. The optics for this type of camera are known and are available at a variety of sizes. The lighting system can be on the inner surface of the side lip of the body of the laryngoscope 115a or on the bottom surface of the body 115b or on both on the inner surface and on the bottom surface of the body 115a and 115b of the laryngoscope. More lights 116 are set on the surface of the retractor 106. The wiring or the fiber optics for the camera are put through the blade from an inlet 240 as shown in FIG. 1B. Fiber optic cables are routed through the blade to the distal tip. An important aspect of the present imaging system is that the camera and the lighting system are synched, such that images are taken with a flashing light and not by a continuous light. The LED lights can trigger a short duration flash light to freeze the motion of the droplets and have a better view of the spray that exits the spray nozzle.

Figure 2B:
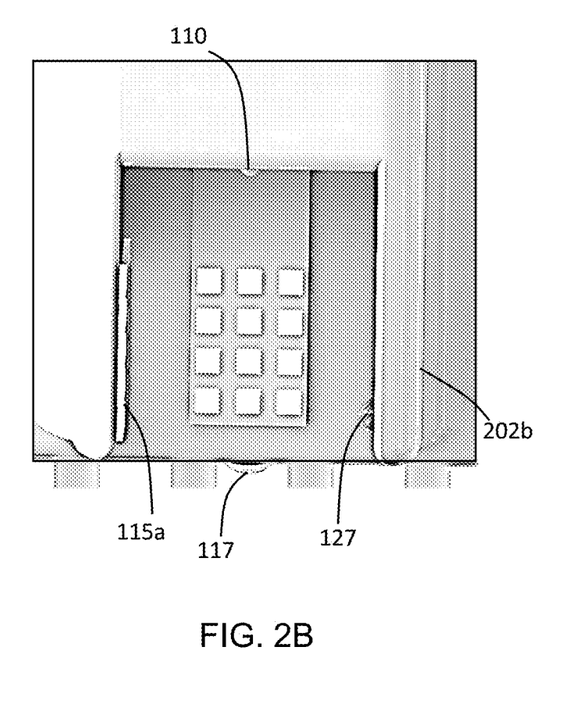
FIG. 2B is a close-up view of a second embodiment of the spatula and the tip of body of the blade of the present anesthetic laryngoscope with the location of the camera being on the sides of the body of the blade.

In another embodiment of the same invention, as illustrated in FIG. 2B, the spray (the first) camera 127 is set on the opposite side of the light 115a and on the lip 202b of the body of the laryngoscope. This arrangement provides more direct view of the droplet size distribution in the spray.

Figure 3:
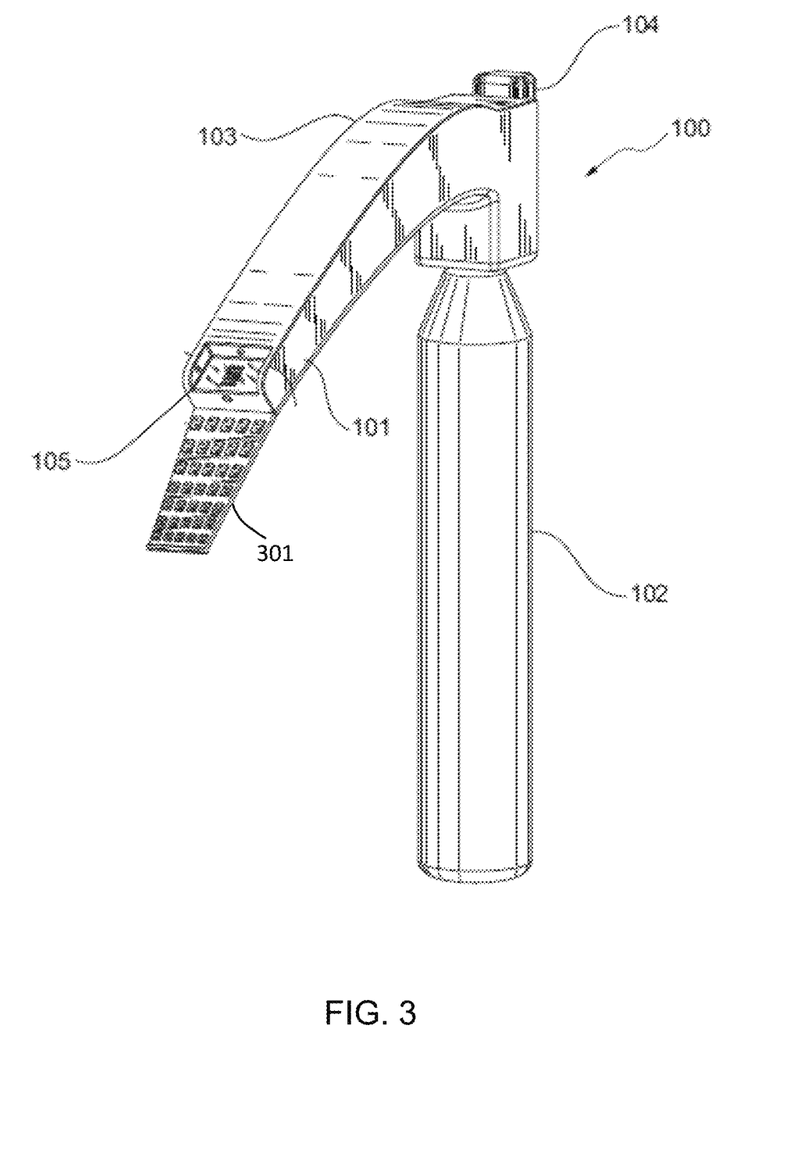
FIG. 3 is another embodiment of the present laryngoscope with a tapered spatula.

In another embodiment of the same invention, the spatula 301 is tapered as illustrated in FIG. 3. The spatula acts as the retractor to manipulate a patient's soft oropharyngeal tissue, such as the tongue. it is recognized that an operable retractor may have other shapes.

Figure 4:
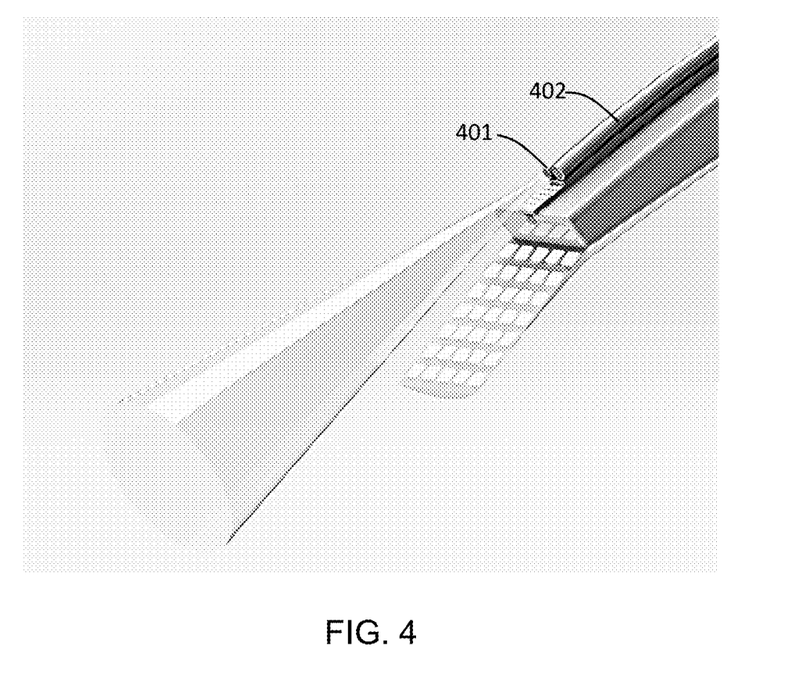
FIG. 4 is another embodiment of the present anesthetic laryngoscope with an anesthetic applicator and imaging system.

In another embodiment of the same invention, the fluid line 401 and the spray camera 402 with its cables are set on the body of the laryngoscope as illustrated in FIG. 4. The spray nozzle is set at the end of the fluid line 402.

Figure 5:
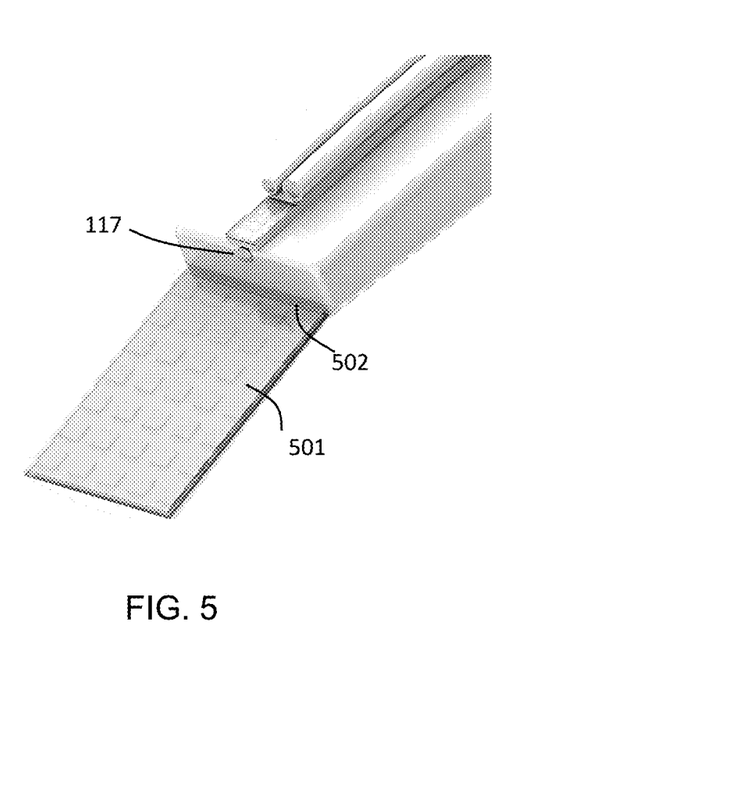
FIG. 5 is another embodiment of the present anesthetic laryngoscope with a transparent cover on the lighting systems.

In another embodiment of the same invention, as illustrated in FIG. 5, the spatula has a light guide 501 to reflect the light 502 that is embedded at the tip of the body of the laryngoscope. This eliminates the need for extra lighting. The surfaces of the light are covered with a transparent material to provide a smooth yet transparent surface.

The present device may be manufactured from a variety of materials appropriate for a medical device, including stainless steel, or injection mold from a medical-grade plastic or plastic-like material, such as polypropylene, polycarbonate, polyvinylchloride, polyurethane, nylon, silicone, rubber, and the like. Such plastic-like material advantageously reduces risk of damage to a patient's teeth resulting from an inadvertent bite-down on the device during an anesthetizing procedure. Furthermore, it is currently preferred to dispose of an anesthetic dispensing assembly, subsequent to a single use, rather than incur the cost and overhead required to sterilize parts for reuse. For this purpose a system using light guide is preferred, wherein the light source is set in the handle and the light is carried through the blade by the light guides.

The operation of the system is illustrated in FIG. 6A-D. A spray 170 comprises of millions of small fluid droplets 180. A spray is characterized by the size distribution of the droplets it generates, a spray angle 190, and the impact surface area, among other parameters. The spray characteristics not only depend on the spray nozzle but on the fluid flow rate and pressure. Currently, practitioners apply a spray of fluid without knowing anything about the size distribution of the droplets, spray angle or the spray impact area. The present device provides such information. In addition, the data gathered on the size distribution together on the effectiveness of the anesthetic (or other fluids) would eventually result in a data that can later be used to allow practitioners to know the spray characteristics that are required for an effective application of the spray. The spray angle 190 may be selected from between about zero degrees and about 45 degrees.

Figure 6A:
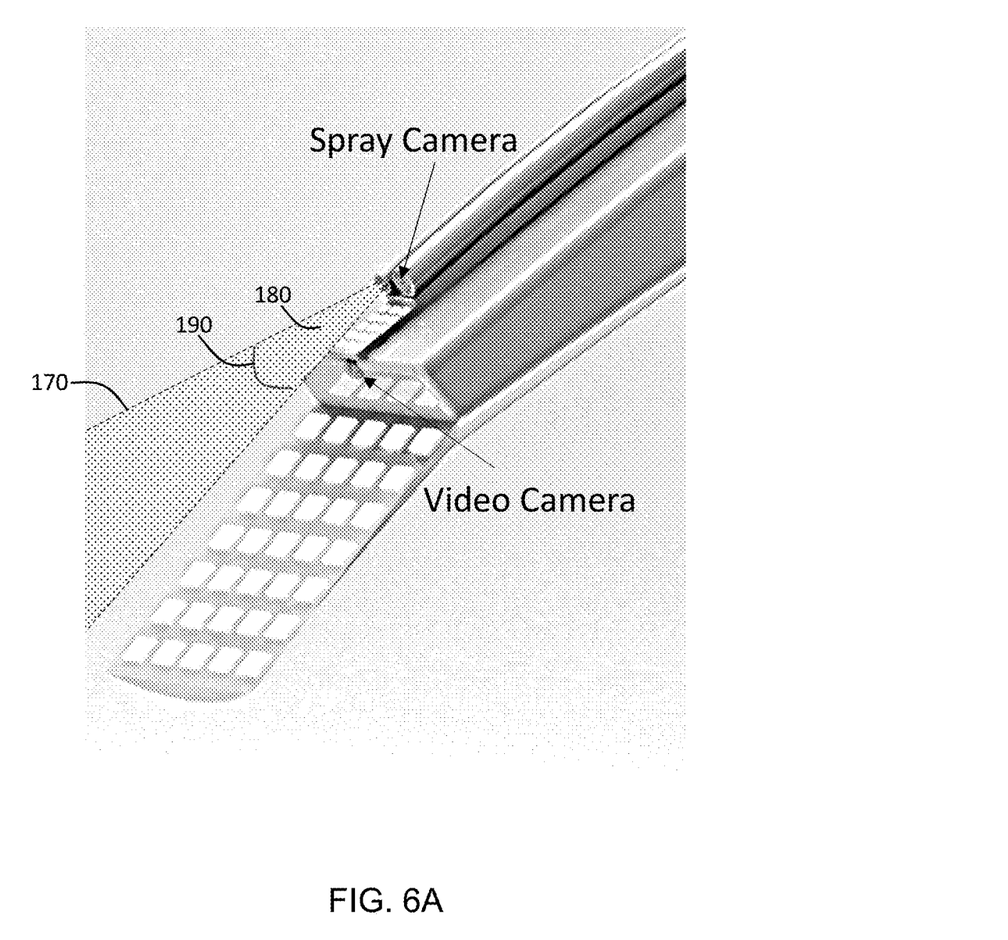
FIG. 6A shows the present device in operation with a spray.
Figure 6B:
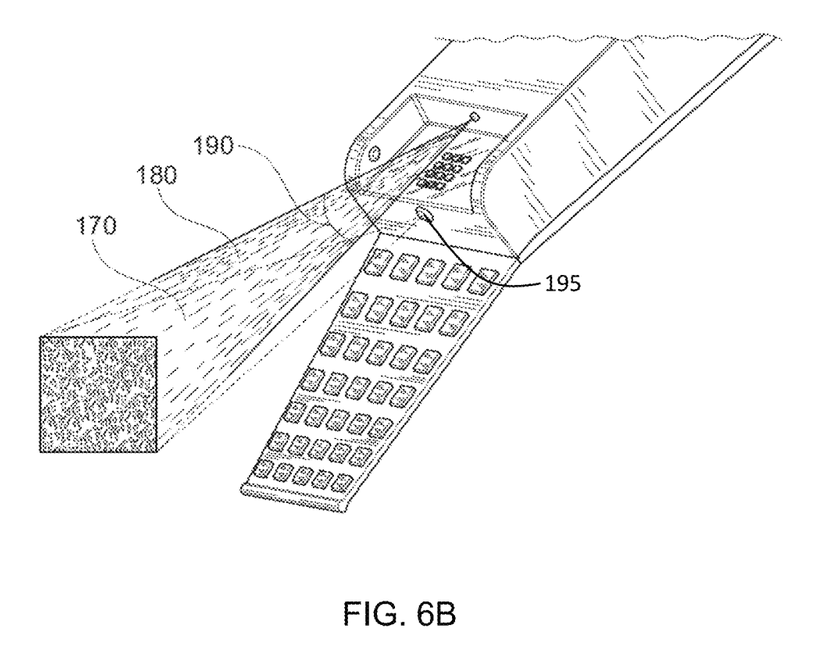
FIG. 6B shows the present device in operation with a spray.
Figure 6C:
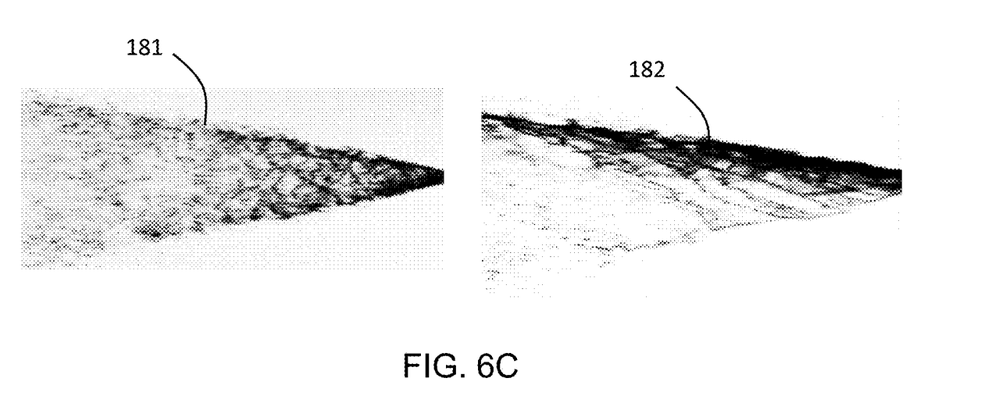
FIG. 6C show the images of an example of good and bad sprays.
Figure 6D:
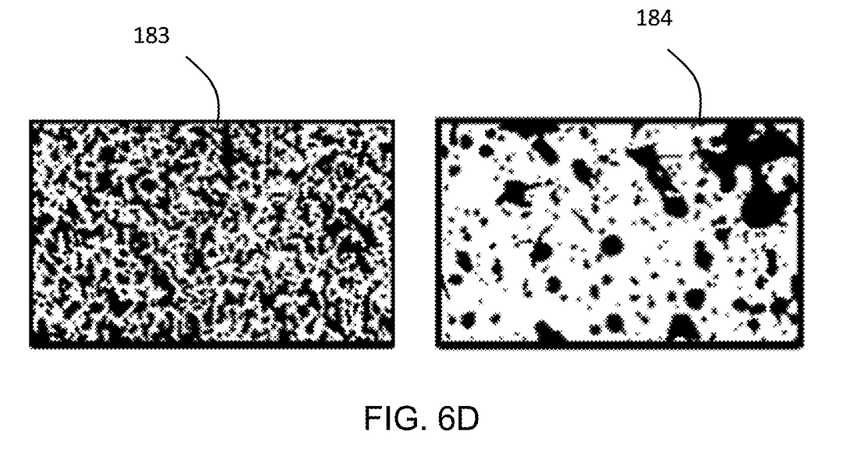
FIG. 6D show the images of an example of good coating and under-coating.

The spray camera has a small focal point with high magnification optics to allow imaging of the close to nozzle spray. This type of imaging can allow a smart algorithm to determine whether the spray is proper. The images obtained by spray camera 120 are sent to a processor. The processor processes the image and compares it with a set of predefined good spray images. If the spray is identified as good, a green light 109a (FIGS. 1B and 1C) at the back 104 of the laryngoscope turns on, letting the operating know that the spray is good. If the spray is identified as bad, a red light 109b at the back 104 of the laryngoscope turns on, letting the operator know that the pressure setting on the syringe needs to be changed. An example of a good 181 and bad 182 sprays are shown in FIG. 6C. A good spray is characterized by a smooth and relatively symmetric gray scale, whereas a bad spray is unsymmetric with large gradients of gray scale. A predefined criterion for the symmetry and gradient variation of the gray scale is set in the imaging algorithm to identify good and bad spray. These parameters can be changed by the practitioner with experience of the practitioner. Similarly, the images on the impact area can show the under- or over-coating of the surface, as shown in FIG. 6D with images 183 as good coating, and 184 ad under-coated. The percentage of the droplet covered areas is an indication of the coating. For example, a 50% coverage area can be good and below 30% is undercoated and above 70% is over-coated. Again, these parameters can be changed by the practitioner for different types of anesthetics.

The processor (not shown) is either embedded inside the body 103 of the laryngoscope or it is an external processor. In one embodiment the laryngoscope connects to a mobile phone, which is in communication with a processor to analyze the images. An app on the mobile phone can show the spray images and identify the good and bad sprays. A second camera 117 for video laryngoscopy is used for viewing the inner parts of the airway and for intubation procedure. In another embodiment shown in FIG. 6B, the second camera 195 set on the distal end of the blade is used to view the impact area. In this configuration, images are obtained using flash photography rather than using view imaging with continuous lighting.

Figure 7:
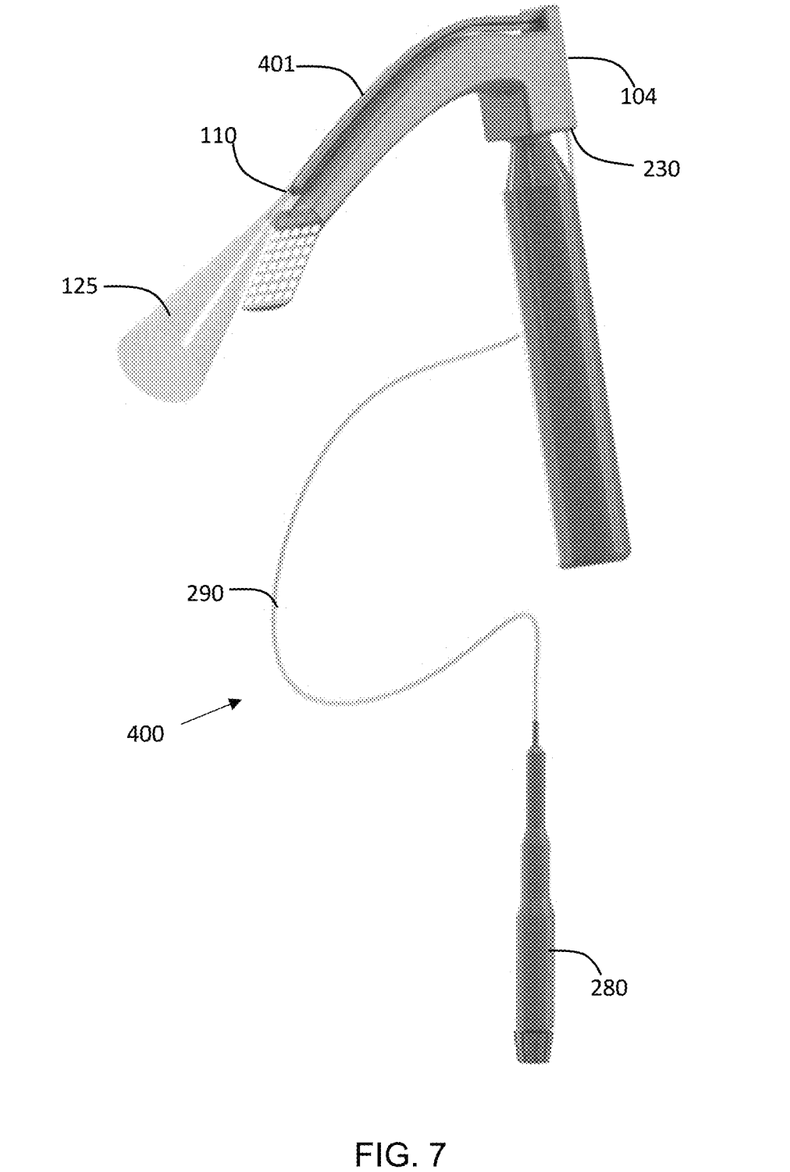
FIG. 7 is a present system including the laryngoscope, and the syringe pump.

In the present embodiment as illustrated in FIG. 7, the dispenser assembly 400 to spray an anesthetic agent comprises of a syringe 280 in combination with a spray nozzle 110 to apply the anesthetic as a mist, or cloud 125. Different types of atomizing nozzles can be used. However, a swirl type nozzle is preferred since it can generate small droplets at low pressures. The spray angle of the swirl nozzle is relatively large, and therefore, it covers a larger area in a short distance from the nozzle. A workable spray angle is believed to be between about 45 degrees.

The spray nozzle 110 is connected to the distal end of a fluid conduit 230 on the laryngoscope that ends at the back side 104 of the laryngoscope. A syringe can be directly or indirectly connected to the conduit inlet through a flexible tubing 290. Workable extension conduit 290 may be formed from medical grade tubing, such as ⅛ inch diameter clear plastic tubing. Such extension conduit is typically transversely flexible, and may be formed into curved shapes.

The handle 102 can have any variation, including grid-enhancing texture, or other structural features to assist a user of the device in manipulating the retractor inside the oral cavity and throat of a patient.

Desirably, the blade 101 is axially curved shape to cooperate with a patient's tongue and/or other oropharyngeal structure operably to permit its insertion through the mouth to dispose the distal tip 108 in approximate registration with the tracheal/esophageal intersection area. The blade 101 and its retractor 106 may be formed in a variety of sizes and shapes to permit selection of a blade 101 that cooperates with the size and shape of a given patient's oropharyngeal structure. One workable shape includes the illustrated substantially constant curvature that may be characterized as approximately forming a quadrant of an ovaloid, such as a circle or shallow ellipse, or a portion of a parabola, or other curve. The handle 102 is then operably connected to a portion of the blade 101 at its proximal end 104. The blade may be removable or foldable attached to the handle.

The blade 101 and its retractor 106 are adapted to manipulate certain oropharyngeal tissue. In general, the retractor 106 is configured for insertion into a patient's mouth, and may be used to press against the patient's tongue, or to manipulate other oropharyngeal tissue during an anesthetizing procedure. Therefore, the retractor 106 desirably includes one or more working surface that is adapted to avoid causing injury to tissue of the patient while contacting such tissue during use of the device. For example, the distal tip 108 is typically blunt, and corners that might come into contact with the patient's tissue are generally rounded. Generally, broad and rounded working surfaces are effective to move tissue out of the way sufficient to permit advancing the distal tip 108 into the patient's throat without damaging the displaced tissue. The working surfaces, such as arcuate ramp, are typically smooth, to facilitate sliding the retractor with respect to oropharyngeal tissue.

In another embodiment of the present invention, the laryngoscope further has a suction tube. The suction tube is attached below the tongue, and connected to a suction system through a flexible tube. The suction system is used when the patient has fluid in the lungs and the system can help in clearing the airway during the process.

Figure 8:
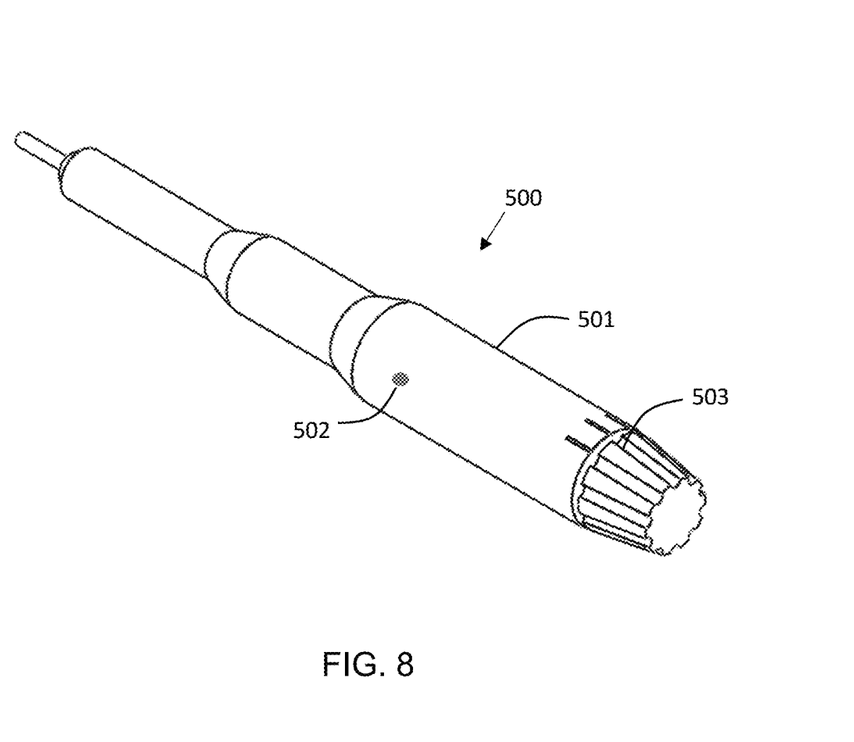
FIG. 8 is the present syringe pump.
Figure 9:
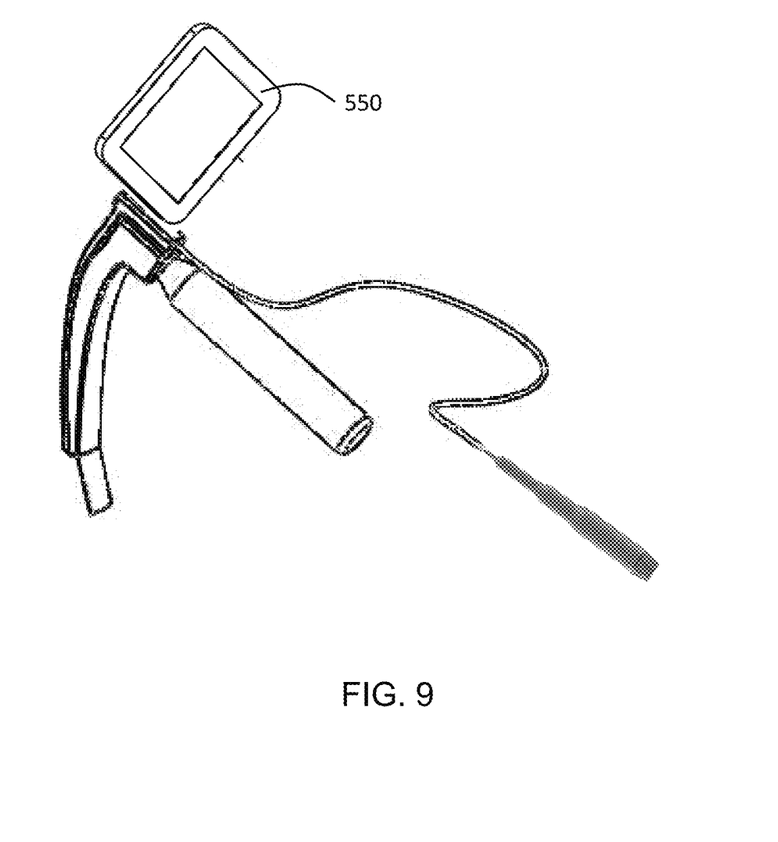
FIG. 9 is a present system including the laryngoscope, the automatic syringe pump and the viewing monitor.

In another embodiment of the present system, an automatic syringe 500, as shown in FIG. 8, is used. The liquid is usually provided by pressing a syringe pump. This does allow for a controlled flow rate and pressure. In order to have a consistent application of anesthetic spray, an automatic syringe pump is provided. The automatic syringe of the present device can dispense a predefined amount of liquid at a predefined pressure. The syringe comprises of a body 501, which can receive a plunger and cylinder to hold a liquid (not shown). The plunger is pushed by a spring-loaded mechanism by push of a button 502 on the body of the syringe. The syringe has a nob 503 that can be turned to change the pressure that can be imparted on the plunger. In operation, the practitioner inserts the blade in the mouth and presses the button on the syringe pump to dispense a spray liquid. The syringe pump is synched with the camera and its flash to take images of the spray as soon as the spray is dispensed and also it takes images of the coated surface. The images are analyzed and a green light tells the practitioner to insert the blade further inside the pathway and apply another dose of anesthetic. This process is repeated until the conscious patient is anesthetized sufficiently to undergo the intubation procedure. The system may have a syringe holder to hold the syringe on the handle for ease of user.

In another embodiment of the present system, the laryngoscope is configured to connect to a video camera as shown in FIG. 9. A video monitor 550 is attachable to the handle to show the images obtained by the video camera 117.

What is claimed is:

1. An anesthetic laryngoscopy system, comprising:

a) a handle;

b) a blade having distal and proximal ends, means for attaching the proximal end of the blade to the handle, said blade having a spatula portion curved longitudinally along its length to be inserted into the mouth of a patient;

c) a fluid dispensing system integrated with said blade and having a spray nozzle to dispense a spray of fluid droplets having a set of spray characteristics;

d) a lighting system disposed on the blade and configured to generate a continuous light and a light flash, the lighting system further comprising an array of light emitting diode (LED) lights on a top surface of the spatula portion;

e) a first camera for video laryngoscopy attached to the blade;

f) a second camera attached to the blade and configured to take a set of images of said spray of fluid droplets, in communication with light flash;

g) a processor having an image processing software to analyze the set of images to determine the set of spray characteristics; and h) an algorithm configured to compare the set of spray characteristics with a set of predefined spray characteristics and to identify a first spray and a second spray, and configured to alert a user to accept the first spray and reject the second spray.

2. The anesthetic laryngoscopy system of claim 1, further having a monitor to show the set of images obtained by the second camera.

3. The anesthetic laryngoscopy system of claim 1, wherein the anesthetic laryngoscopy system configured to connect to a mobile phone and the mobile phone acts as a video laryngoscopy.

4. The anesthetic laryngoscopy system of claim 1, wherein the blade comprising of a groove section that has a front step, a first side lip and a second side lip, and wherein the spray nozzle and the second camera are on the front step.

5. The anesthetic laryngoscopy system of claim 1, wherein the fluid dispensing system and the lighting system are disposed on a top surface of the blade.

6. The anesthetic laryngoscopy system of claim 1, wherein the processor is imbedded in at least one of a body of the blade, in the handle, and in an external device.

7. The anesthetic laryngoscopy system of claim 1, wherein the lighting system comprising of a light source that transmits light through a light guide disposed on the spatula, thereby illuminating the whole spatula.

8. The anesthetic laryngoscopy system of claim 1, wherein the spray nozzle is a swirl nozzle.

9. The anesthetic laryngoscopy system of claim 1, further having a syringe holder to hold a syringe containing a fluid to be dispensed and to control a dose of a fluid by depressing a plunger of the syringe.

10. The anesthetic laryngoscopy system of claim 1, wherein the spray nozzle is movably attached to the blade to change the direction of the spray.

11. The anesthetic laryngoscopy system of claim 1, wherein the processor is configured to analyze the images of a spray impact area to determine an application amount of an anesthetic fluid, and to alert if the application amount of the anesthetic fluid is according to a predetermined amount or not.

12. The anesthetic laryngoscopy system of claim 1, wherein the lighting system comprises of a light source and a set of fiber optics that carry the light from the light source to the distal end of the blade.

13. The anesthetic laryngoscopy system of claim 1, wherein the handle is configured to receive a set of batteries.

14. The anesthetic laryngoscopy system of claim 1, wherein the first spray is identified as having a substantially symmetric gray scale image, and the second spray is identified as having a substantially unsymmetric gray scale image.

15. The anesthetic laryngoscopy system of claim 1, wherein the blade comprising of a groove section that has a front step, a first side lip and a second side lip, and wherein the spray nozzle is located on the front step, the second camera is on the first side lip and a lighting source is on the second side lip opposing the second camera.

16. The anesthetic laryngoscopy system of claim 1, wherein the blade comprising of a groove section having a proximal groove end and distal groove end, and wherein the proximal groove end has a first step and the distal groove end has a second step, and the groove has a first side lip and a second side lip extending from the proximal groove end to the distal groove end, and wherein the spatula portion is attached to the distal groove end of the groove section, and wherein the spray nozzle is on the first step, the first camera is on the second step, the second camera is on the first side lip and the lighting source is on the second side lip opposing the second camera.

17. The anesthetic laryngoscopy system of claim 1, wherein the fluid dispensing system comprises of an anesthetic fluid.

* * * * *